(12) United States Patent
Smid et al.

(10) Patent No.: US 8,575,148 B2
(45) Date of Patent: Nov. 5, 2013

(54) SPIRO AZEPANE-OXAZOLIDINONES AS KV1.3 POTASSIUM CHANNEL BLOCKERS

(75) Inventors: Pieter Smid, Weesp (NL); Michael Mlinaric, Hannover (DE); Konrad F. Koehler, Huddinge (SE); Sara Nuñez Garcia, Weesp (NL); Elmar Wegener, Hannover (DE); Josephus H. M. Lange, Weesp (NL)

(73) Assignee: Abbott Healthcare Products B.V., Weesp (NL)

( * ) Notice: Subject to any disclaimer, the term of this patent is extended or adjusted under 35 U.S.C. 154(b) by 233 days.

(21) Appl. No.: 13/133,042

(22) PCT Filed: Dec. 10, 2009

(86) PCT No.: PCT/EP2009/066836
§ 371 (c)(1),
(2), (4) Date: Jun. 6, 2011

(87) PCT Pub. No.: WO2010/066840
PCT Pub. Date: Jun. 17, 2010

(65) Prior Publication Data
US 2011/0237569 A1    Sep. 29, 2011

Related U.S. Application Data

(60) Provisional application No. 61/121,913, filed on Dec. 12, 2008.

(30) Foreign Application Priority Data

Dec. 12, 2008  (EP) ..................... 08171421

(51) Int. Cl.
*A61P 3/10*     (2006.01)
*A61P 29/00*    (2006.01)
*A61K 31/55*    (2006.01)
*C07D 498/10*   (2006.01)

(52) U.S. Cl.
USPC ................ 514/212.02; 514/217.11; 540/543; 540/604

(58) Field of Classification Search
USPC ................ 514/212.02, 217.11; 540/543, 604
See application file for complete search history.

(56) References Cited

FOREIGN PATENT DOCUMENTS

WO   WO 00/25786   5/2000

OTHER PUBLICATIONS

Chemical Abstracts Registry No. 1041261-12-4, indexed in the Registry file on STN CAS Online Aug. 15, 2008.*
Chemical Abstracts Registry No. 1041074-93-4, indexed in the Registry file on STN CAS Online Aug. 15, 2008.*
Chemical Abstracts Registry No. 1041074-81-0, indexed in the Registry file on STN CAS Online Aug. 15, 2008.*
Chemical Abstracts Registry No. 1041261-13-5, indexed in the Registry file on STN CAS Online Aug. 15, 2008.*
Harvey et al., "A New Class of Blockers of the Voltage-Gated Potassium Channel Kv1.3 via Modification of the 4- or 7-Position of Khellinone," *Journal of Medicinal Chemistry*, Feb. 23, 2006, vol. 49, No. 4, pp. 1433-1441.
Baell, "Potassium Channel Blockers as Immunosuppressants," *Expert Opinion on Therapeutic Patents*, Sep. 2005, vol. 15, No. 9, pp. 1209-1220.
Schmalhoffer et al., "Identification of a New Class of Inhibitors of the Voltage-Gated Potassium Channel, K1.3, with Immunosuppresenant Properties," *Biochemistry*, Jun. 18, 2011, vol. 4, No. 24, pp. 7781-7794, XP002523189.
International Search Report issued on Apr. 3, 2010, in PCT/EP2009/066836.

* cited by examiner

*Primary Examiner* — Brenda Coleman
(74) *Attorney, Agent, or Firm* — Finnegan, Henderson, Farabow, Garrett & Dunner LLP

(57) ABSTRACT

This invention concerns spiro azepane-ox-azolidinones as voltage gated Kv1.3 potassium channel blockers, pharmaceutical compositions containing these compounds, methods for preparing the compounds, methods for preparing novel intermediates useful for their synthesis, and methods for preparing compositions. The invention also relates to the uses of such compounds and compositions, particularly their use in administering them to patients to achieve a therapeutic effect in the treatment of diabetes, psoriasis, obesity, transplant rejection and inflammatory neuropathies, including T-cell mediated autoimmune diseases such as rheumatoid arthritis and multiple sclerosis. The compounds have formula (1):

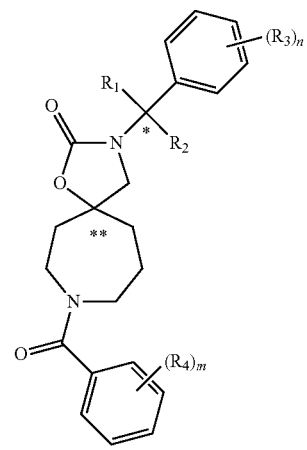

wherein $R_1$, $R_2$, $(R_3)_n$, and $(R_4)_m$ have the meanings given in the specification.

14 Claims, No Drawings

SPIRO AZEPANE-OXAZOLIDINONES AS KV1.3 POTASSIUM CHANNEL BLOCKERS

This application is a National Stage application under 35 U.S.C. §371 of International Application No. PCT/EP2009/066836, filed Dec. 10, 2009, and claims the benefit of priority of European Application No. 08171421.4, filed Dec. 12, 2008, and U.S. Provisional Application No. 61/121,913, filed Dec. 12, 2008, the content of each of which is incorporated herein by reference.

TECHNICAL FIELD

This invention relates to the fields of pharmaceutical and organic chemistry. Embodiments of the present invention relate to, and provide spiro azepane-oxazolidinones(1-oxa-3,8-diazaspiro-[4.6]undecan-2-ones) as voltage gated Kv1.3 potassium channel blockers, and intermediates, formulations and methods.

BACKGROUND

Blockers of voltage gated Kv1.3 potassium channels based on the benzamidomethylene-cyclohexyl scaffold were disclosed in WO 00/25786 (Merck & Co., 2000), by Schmalhofer et al. (Biochemistry, 41, 7781-7794, 2002), by Baell (Expert Opin. Ther. Patents, 15(9), 1209-1220, 2005) and Harvey (J. Med. Chem., 49(4), 1433-1441, 2006).

DISCLOSURE

It was found that substituted spiro azepane-oxazolidinones (1-oxa-3,8-diazaspiro[4.6]undecan-2-ones) are novel voltage gated Kv1.3 potassium channel blockers. This invention relates to a compound of formula (1), or a tautomer, stereoisomer, or a pharmacologically acceptable salt of any of the foregoing,

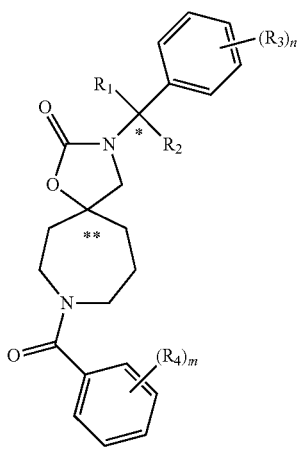

(1)

wherein:
$R_1$ and $R_2$ independently are hydrogen, deuterium, fluorine, $CF_3$ or alkyl($C_{1-3}$), unsubstituted or substituted with one or more fluorine atoms,
n is 0 (zero), 1 or 2,
$R_3$ is chosen from halogen, alkyl($C_{1-3}$), $CF_3$, CN, $NH_2$, NHAc, OH, $OCH_3$, or $OCF_3$
m is 0 (zero), 1, 2 or 3,
$R_4$ is chosen from halogen, alkyl($C_{1-3}$), $CF_3$, CN, $NH_2$, NHAc, OH, $OCH_3$, or $OCF_3$, or $(R_4)_m$ and the phenyl ring to which it is attached form a naphthyl group.

The invention also relates, in some embodiments, to a compound of formula (1), or a tautomer, stereoisomer, or a pharmacologically acceptable salt of any of the foregoing, wherein $R_1$ and $R_2$ independently are hydrogen or methyl, n is 0 (zero) or 1, $R_3$ is halogen, m is 1 or 2, and $R_4$ is chosen from halogen, $CF_3$, CN, $OCH_3$, or $OCF_3$, or $(R_4)_m$ and the phenyl ring to which it is attached form a naphthyl group.

Other embodiments provide one or more compounds of formula (1) or a tautomer, stereoisomer, or a pharmacologically acceptable salt of any of the foregoing, wherein $R_1$ and $R_2$ independently are hydrogen, deuterium, fluorine, $CF_3$ or alkyl($C_{1-3}$), unsubstituted or substituted with on or more fluorine atoms; n is 0 (zero), 1 or 2; $R_3$ is chosen from halogen, alkyl($C_{1-3}$), $CF_3$, CN, $NH_2$, NHAc, OH, $OCH_3$, or $OCF_3$; m is 0 (zero), 1, 2 or 3; $R_4$ is chosen from halogen, alkyl($C_{1-3}$), $CF_3$, CN, $NH_2$, NHAc, OH, $OCH_3$, or $OCF_3$, or $(R_4)_m$ and the phenyl ring to which it is attached form a naphthyl group.

The invention also relates, in some embodiments, to a compound of formula (1), or a tautomer, stereoisomer, or a pharmacologically acceptable salt of any of the foregoing, wherein $R_1$ and $R_2$ independently are hydrogen or methyl, n is 0 (zero) or 1, $R_3$ is halogen, m is 1 or 2, and $R_4$ is chosen from halogen, $CF_3$, CN, $OCH_3$, or $OCF_3$, or $(R_4)_m$ and the phenyl ring to which it is attached form a naphthyl group.

Further embodiments provide compounds of formula (1) or a tautomer, stereoisomer, or a pharmacologically acceptable salt of any of the foregoing, selected from:

(5S)-8-[3,5-bis(trifluoromethyl)benzoyl]-3-[(1S)-1-phenylethyl]-1-oxa-3,8-diazaspiro[4.6]-undecan-2-one (5R)-8-[3,5-bis(trifluoromethyl)benzoyl]-3-[(1S)-1-phenylethyl]-1-oxa-3,8-diazaspiro[4.6]-undecan-2-one (5R)-8-[3,5-bis(trifluoromethyl)benzoyl]-3-[(1R)-1-phenylethyl]-1-oxa-3,8-diazaspiro[4.6]-undecan-2-one (5S)-8-[3,5-bis(trifluoromethyl)benzoyl]-3-[(1R)-1-phenylethyl]-1-oxa-3,8-diazaspiro[4.6]-undecan-2-one (5S)-8-[3-cyanobenzoyl]-3-[(1S)-1-phenylethyl]-1-oxa-3,8-diazaspiro[4.6]undecan-2-one (5R)-8-[3-cyanobenzoyl]-3-[(1S)-1-phenylethyl]-1-oxa-3,8-diazaspiro[4.6]undecan-2-one (5R)-8-[3-cyanobenzoyl]-3-[(1R)-1-phenylethyl]-1-oxa-3,8-diazaspiro[4.6]undecan-2-one (5S)-8-[3-cyanobenzoyl]-3-[(1R)-1-phenylethyl]-1-oxa-3,8-diazaspiro[4.6]undecan-2-one Other embodiments provide one or more compounds of formula (1) or a pharmacologically acceptable salt thereof, said compound being an optically active enantiomer or diastereoisomer.

The invention also relates, in some embodiments, to a compound of formula (1) or a pharmacologically acceptable salt thereof, wherein the carbon atom attached to the nitrogen atom of the oxazolinone ring is the (R) or (S) enantiomer.

The invention also relates, in some embodiments, to a compound of formula (1) or a pharmacologically acceptable salt thereof, wherein the central quaternary spiro-carbon atom is the (R) or (S) enantiomer.

Other embodiments of the invention relate to compounds of formulae (v), (vi) or (vii)

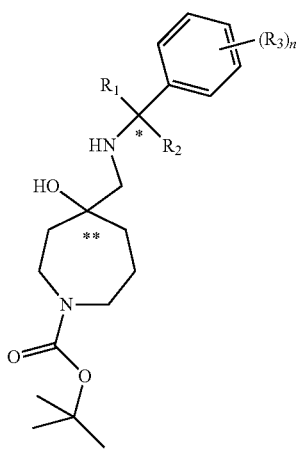

(v)

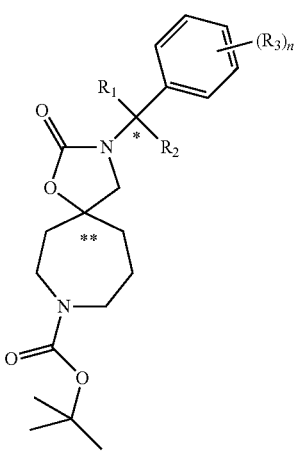

(vi)

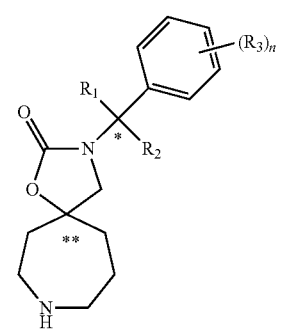

(vii)

wherein $R_1$, $R_2$, n and $R_3$ have the meanings as given above, such compounds being useful in the synthesis of compounds of formula (1).

Another embodiment provides the compound:

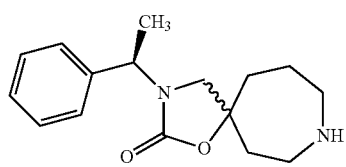 [SMILES: C[C@H](c1ccccc1)N1CC2(CCCNCC2)OC1=O]

Another embodiment provides a process to prepare compounds of formula (1), comprising the steps of:

(i) protecting the amino group of hexahydro(1H)-azepin-4-one 1 with a protecting group, yielding a ketone of formula 2:

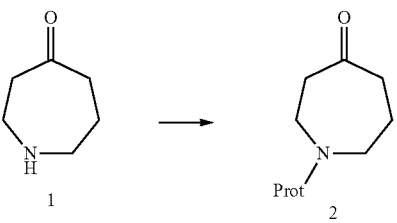

(ii) epoxidizing the ketone of formula 2 to a spiro-epoxide of formula 3:

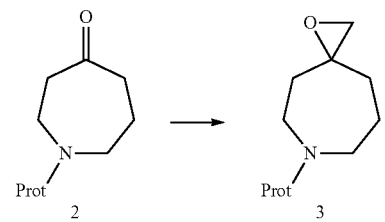

(iii) aminolysis of the spiro-epoxide of formula 3, with an amine 4 of formula $RNH_2$, wherein R represents the moiety:

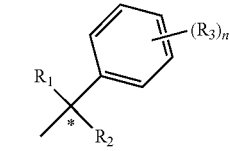

wherein $R_1$ and $R_2$ independently are hydrogen, deuterium, fluorine, $CF_3$ or alkyl($C_{1-3}$), unsubstituted or substituted with on or more fluorine atoms; n is 0 (zero), 1 or 2; $R_3$ is chosen from halogen, alkyl($C_{1-3}$), $CF_3$, CN, $NH_2$, NHAc, OH, $OCH_3$, or $OCF_3$; m is 0 (zero), 1, 2 or 3, to yield an aminoalcohol of formula 5:

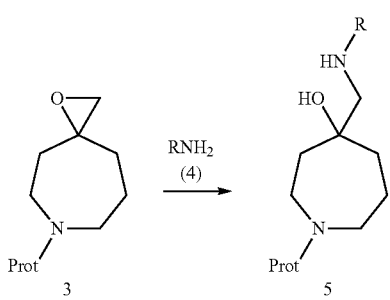

(iv) ringclosure of the aminoalcohol 5 in the presence of a carbonylating agent, catalyzed by DMAP, to the spiro-oxazolidinone derivative 6

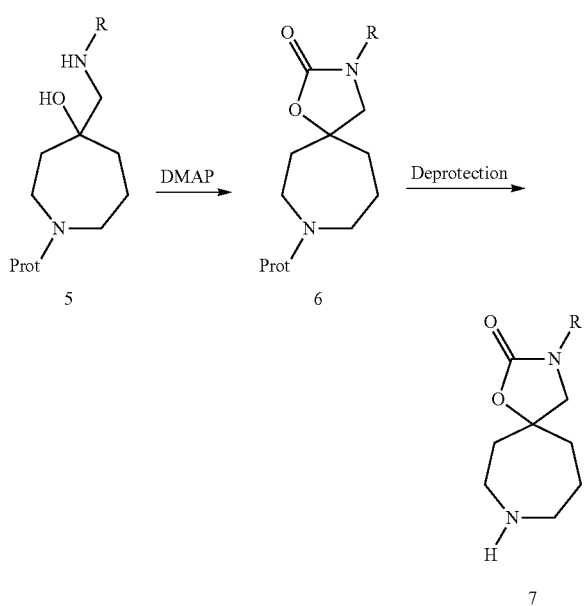

(v) deprotecting the spiro-oxazolidinone of formula 6, yielding a compound of formula 7.

Specific embodiments provide the process given above wherein said protecting group is chosen from a benzyloxycarbonyl (Cbz) or a tert-butoxycarbonyl (t-Boc) group.

Other embodiments provide a medicament, comprising a compound of formula (1), or a pharmacologically acceptable salt thereof.

Further embodiments provide a compound of formula (1) for use in treating diabetes, psoriasis, obesity, transplant rejection and inflammatory neuropathies, including T-cell mediated autoimmune diseases such as rheumatoid arthritis and multiple sclerosis.

The invention also relates, in some embodiments, to a pharmaceutical composition comprising, at least one pharmaceutically acceptable carrier, or at least one pharmaceutically acceptable auxiliary substance, or a combination of two or more thereof; and a pharmacologically active amount of at least one compound of formula (1), or a pharmacologically acceptable salt thereof.

Further embodiments provide one the use of a compound of formula (1), to prepare a pharmaceutical composition for treating diabetes, psoriasis, obesity, transplant rejection, and inflammatory neuropathies, including T-cell mediated autoimmune diseases such as rheumatoid arthritis and multiple sclerosis.

Other embodiments of the invention include:
methods for treating diabetes, psoriasis, obesity, transplant rejection, and inflammatory neuropathies, including T-cell mediated autoimmune diseases such as rheumatoid arthritis and multiple sclerosis, the methods comprising administering to a patient in need of such treating a compound of formula (1).

methods of blocking Kv1.3 potassium channels comprising administering to a subject in need thereof, an pharmaceutically effective amount of a compound of formula (1);

The invention further relates to combination therapies comprising a compound of formula (1), or a pharmaceutical composition or formulation comprising a compound of formula (1), is administered concurrently or sequentially or as a combined preparation with another therapeutic agent or agents, for treating one or more of the conditions listed above.

Such other therapeutic agent(s) may be administered prior to, simultaneously with, or following the administration of the compounds of the invention.

The invention also provides compounds, pharmaceutical compositions, kits and methods for treating diabetes, psoriasis, obesity, transplant rejection, and inflammatory neuropathies, including T-cell mediated autoimmune diseases such as rheumatoid arthritis and multiple sclerosis, the method comprising administering to a patient in need of such treating a compound of formula (1).

The compounds of the invention possess Kv1.3 potassium channel blocking activity. The inhibiting activities of the compounds of the invention can be readily demonstrated, for example, using one or more of the assays described herein or known in the art.

The invention also provides methods of preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers. All compounds of the present invention do contain at least one chiral center at their quaternary spiro-carbon atom. A chiral with unknown absolute chirality is named 'conf 1' or 'configuration 1', and the other enantiomer 'conf 2' or 'configuration 2'. 'Conf(iguration) 1' and 'conf(iguration) 2' can correlate to the (R) or the (S) assignments respectively, on conversely to the (S) or (R).

Depending on the nature of the various substituents, the molecule can have additional asymmetric centers. Each such asymmetric center will independently produce two optical isomers. All of the possible optical isomers, enantiomers and diastereomers, in mixtures and as pure or partially purified compounds, belong to this invention. The present invention comprehends all such isomeric forms of these compounds. Formula (1) shows the structure of the class of compounds without preferred stereochemistry. The independent syntheses of these optical isomers, or their chromatographic separations, may be achieved as known in the art by appropriate modification of the methodology disclosed therein. Their absolute stereochemistry may be determined by the X-ray crystallography of crystalline products or crystalline intermediates, which are derivatized, if necessary, with a reagent containing an asymmetric center of known absolute configuration. Racemic mixtures of the compounds can be separated into the individual enantiomers by methods well-known in the art, such as the coupling of a racemic mixture of compounds to an enantiomerically pure compound to form a diastereomeric mixture, followed by separation of the individual diastereomers by standard methods, such as fractional crystallization or chromatography. The racemic mixture of the compounds can also be separated directly by chromatographic methods utilizing chiral stationary phases, which are well-known in the art. Alternatively, any enantiomer of a compound may be obtained by stereoselective synthesis using optically pure starting materials or reagents of known configuration by methods well-known in the art.

Cis and trans isomers of the compound of formula (1), or a pharmaceutically acceptable salt thereof, also belong to the invention, and this also applies to tautomers of the compounds of formula (1).

Some of the crystalline forms for the compounds may exist as polymorphs, and as such are intended to be included in the invention. Compound of formula (1) isotopically-labeled to be detectable by PET or SPECT, also fall within the scope of the invention. The same applies to compounds of formula (1) labeled with [$^{13}$C]—, [$^{14}$C]—, [$^{3}$H]—, [$^{18}$F]—, [$^{125}$I]— or other isotopically enriched atoms, suitable for receptor binding or metabolism studies.

The compounds of the invention may also be used as reagents or standards in the biochemical study of neurological function, dysfunction and disease.

DEFINITIONS

General terms used in the description of compounds herein disclosed bear their usual meanings. The term alkyl as used herein denotes a univalent saturated, branched or straight, hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl, octadecyl, etc. When qualified 'lower', the alkyl group will contain from 1 to 6 carbon atoms. The same carbon content applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_{x-y}$ defines the number of carbon atoms present from the integer "x" to the integer "y" inclusive. 'Alkyl($C_{1-3}$)' for example, includes methyl, ethyl, n-propyl or isopropyl, and 'alkyl($C_{1-4}$)' includes 'methyl, ethyl, n-propyl, isopropyl, n-butyl, 2-butyl, isobutyl or tert-butyl'.

'Halo' or 'Halogen' refers to chloro, fluoro, bromo or iodo; 'hetero' as in 'heteroalkyl, heteroaromatic', etc. includes containing one or more N, O or S atoms. 'heteroalkyl' includes alkyl groups with heteroatoms in any position, thus including N-bound O-bound or S-bound alkyl groups.

The term "substituted" means that the specified group or moiety bears one or more substituents. Where any group may carry multiple substituents, and a variety of possible substituents can be provided, the substituents are independently selected, and need not to be the same. The term "unsubstituted" means that the specified group bears no substituents. With reference to substituents, the term "independently" means that when more than one of such substituents are possible, they may be the same or different from each other.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. To provide a more concise description, the terms 'compound' or 'compounds' include tautomers, stereoisomers, or pharmacologically acceptable salts, also when not explicitly mentioned.

'Form' is a term encompassing all solids: polymorphs, solvates, amorphous forms. 'Crystal form' refers to various solid forms of the same compound, for example polymorphs, solvates and amorphous forms. 'Cocrystals' are multicomponent crystals with a unique lattice: new chemical species produced with neutral compounds. 'Amorphous forms' are non-crystalline materials with no long range order, and generally do not give a distinctive powder X-ray diffraction pattern. Crystal forms in general have been described by Byrn (*Pharmaceutical Research*, 12(7), 945-954, 1995) and Martin ("Remington: The Science and Practice of Pharmacy", Mack Publishing Company, 19$^{th}$ Edition, Easton, Pa., Vol 2., Chapter 83, 1447-1462, 1995). 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to experimental or measurement conditions for such given value.

Throughout the description and the claims of this specification the word "comprise" and variations of the word, such as "comprising" and "comprises" is not intended to exclude other additives, components, integers or steps.

While it may be possible for the compounds of formula (1) to be administered as the raw chemical, it is preferable to present them as a 'pharmaceutical composition'. According to a further aspect, the present invention provides a pharmaceutical composition comprising at least one compound of formula (1), at least one pharmaceutically acceptable salt thereof, or a mixture of any of the foregoing, together with one or more pharmaceutically acceptable carriers thereof, and with or without one or more other therapeutic ingredients. The carrier(s) must be 'acceptable' in the sense of being compatible with the other ingredients of the formulation and not deleterious to the recipient thereof. The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Within the context of this application, the term 'combination preparation' comprises both true combinations, meaning a compound of formula (1) and one or more other medicaments physically combined in one preparation such as a tablet or injection fluid, as well as 'kit-of-parts', comprising a compound of formula (1) and one or more other medicaments in separate dosage forms, together with instructions for use, with or without further means for facilitating compliance with the administration of the component compounds, e.g. label or drawings. With true combinations, the pharmacotherapy by definition is simultaneous. The contents of 'kit-of-parts', can be administered either simultaneously or at different time intervals. Therapy being either concomitant or sequential will be dependant on the characteristics of the other medicaments used, characteristics such as onset and duration of action, plasma levels, clearance, etc., as well as on the disease, its stage, and characteristics of the individual patient.

Dose. The potency of the compounds of the invention as inhibitors of voltage gated Kv1.3 channels was determined below. From the potency measured for a given compound of formula (1), one can estimate a theoretical lowest effective dose. At a concentration of the compound equal to twice the measured inhibition constant, nearly 100% of the Kv1.3 channels will be blocked by the compound. By converting that concentration to mg of compound per kg of patient one obtains a theoretical lowest effective dose, assuming ideal bioavailability. Pharmacokinetic, pharmacodynamic, and other considerations may alter the dose actually administered to a higher or lower value. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administering a composition of the invention. That amount includes the amount sufficient to exhibit a detectable therapeutic or ameliorative response in a tissue system, animal or human. The effect may include, for example, treating the conditions listed herein. The precise pharmaceutically effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact pharmaceutically effective amount in advance. A "pharmaceutical salt" refers to an acid:base complex containing an active pharmaceutical ingredient (API) along with additional non-toxic molecular species in the same crystal structure. The term "pharmaceutically acceptable salt" refers to those salts that are, within the scope of sound medical judgment, suitable for use in contact with the tissues of humans and lower animals without undue toxicity, irritation, allergic response, etc., and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, S. M.: "*Pharmaceutical salts*", *J. Pharmaceutical Science*, 66, 1-19 (1977). Common anions used in pharmaceutically acceptable salts include: chloride, bromide, sulfate, nitrate, phosphate, bicarbonate, mesylate, esylate, isothianate, tosylate, napsylate, besylate, acetate, propionate, maleate, benzoate, salicylate, fumarate, citrate, lactate, maleate, tartrate, pamoate, succinate, glycolate, hexanoate, octanoate, decanoate, stearate, oleate, aspartate and glutamate. Common cations used as counterions in pharmaceutically acceptable salts include: sodium, potassium, calcium, magnesium, lithium, zinc, aluminum, arginine, lysine, histidine, triethylamine, ethanolamine, triethanolamine, ethilenediamine, meglumine, procaine and benzathine.

The 'free base' form may be regenerated by contacting the salt with a base or acid, and isolating the parent compound in the conventional matter. The parent form of the compound differs from the various salt forms in certain physical properties, such as solubility in polar solvents, but otherwise the salts are equivalent to the parent form of the compound for the purposes of the present invention.

The term "treatment" as used herein refers to any treatment of a human condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes restraining, alleviating, ameliorating, and slowing, stopping or reversing progression, severity, or a resultant symptom. As used herein, the term "medical therapy" intendeds to include diagnostic and therapeutic regimens carried out in vivo or ex vivo on humans.

EXAMPLE 1

Analytical Methods

Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H; 125.7 MHz for $^{13}$C; 50.7 Mhz, 470.4 MHz for $^{19}$F) using a 5 mm SW probe. The spectra were determined in deuterated chloroform or dichloromethane obtained from Cambridge Isotope Laboratories Ltd. Chemical shifts (δ) are given in ppm downfield from tetramethylsilane ($^1$H, $^{13}$C) or CCl$_3$F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of $D_2O$.

Flash chromatography refers to purification using the indicated eluent and silica gel (either Acros: 0.030-0.075 mm or Merck silica gel 60: 0.040-0.063 mm).

Column chromatography was performed using silica gel 60 (0.063-0.200 mm, Merck).

Melting points were recorded on a Büchi B-545 melting point apparatus.

Reactions were monitored by using thin-layer chromatography (TLC) on silica coated plastic sheets (Merck precoated silica gel 60 F254) with the indicated eluent. Spots were visualised by UV light (254 nm) or $I_2$.

Mass spectra and accurate masses were measured with a JEOL JMS-SX/SX 102 A Tandem Mass Spectrometer using Fast Atom Bombardement (FAB). A resolving power of 10,000 (10% valley definition) for high resolution FAB mass spectrometry was used.

Analytical HPLC was performed on a C18 column (Inertsil ODS-3, particle size 3 mm; 4.6 mm 50 mm) using the following elution gradient: linear gradient of 5% to 95% aqueous $CH_3CN$ containing 0.04% $HCO_2H$ over 5 min, then 95% aqueous $CH_3CN$ containing 0.04% $HCO_2H$ for 2 min at 2.0 ml $min^{-1}$. Products were detected at $\lambda=254$ nm.

Liquid Chromatography-Mass Spectrometrry (LC-MS): "Method W"

The LC-MS system consisted of a Waters 1525µ pump, connected to a Waters 2777 auto sampler. The LC methode was:

| step | total time | flow (µl/min) | A (%) | B (%) |
|---|---|---|---|---|
| 0 | 0.2 | 1600 | 90 | 10 |
| 1 | 2.5 | 1600 | 0 | 100 |
| 2 | 2.8 | 1600 | 0 | 100 |
| 3 | 2.9 | 1600 | 90 | 10 |
| 4 | 3.10 | 1600 | 90 | 10 |
| 5 | 3.11 | 500 | 90 | 10 |

A = 100% water with 0.2% HCOOH;
B = 100% acetonitrile with 0.2% HCOOH

The auto sampler had a 10 µl injection loop, the injection volume was 10 µl. The auto sampler was connected to a Waters Sunfire C18 30*4.6 mm column with 2.5 um particles. The column was thermostated at room temperature (about 23° C.). The column was connected to a Waters 2996 PDA. The wavelength was scanned from 240 to 320 nm. The resolution was 1.2 nm and the sampling rate was 20 Hz. After the PDA, the flow was split 1:1 and connected to a Waters 2424 ELSD, having the following parameters: gas pressure: 40 psi; data rate 20 points/sec; gain 500; time constant 0.2 sec; nebulizer mode cooling; drift tube 50° C.

Samples were also measured with a Waters ZQ mass detector. The mass spectrometer had the following parameters: scanrange: 117-900 a.m.u.; polarity: positive; data format: centroid; time per scan: 0.500 sec; interscan time: 0.05 sec; capillary 2.5 kV; cone 25 V; extractor 2 V; RF lens 0.5 V; source temp 125° C.; desolvation temp 400 C; cone gas 100 L/Hr; desolvation gas 800 L/Hr; LM 1 Resolution 15; HM 1 Resolution 15; ion energy 0.5; multiplier 500 V. The complete system was controlled by Masslynx 4.1.

Liquid Chromatography-Mass Spectrometry (LC-MS): "Method H"
Instrument: Alliance HT 2795, Waters
  Photodiode Array Detector 2996, Waters
  ZQ Single Quad, Waters/micromass
  PL-ELS 1000 Lightscattering-Detector, Polymer Labs
LC parameters:
Column XTerra MS C18, 2.5 µm, 50×4.6 mm, Waters
Guard-Column XTerra MS C18, 3.5 µm, 10×2.1 mm, Waters
Solvent A 0.01 M NH4Ac pH 5.0+5% acetonitrile
Solvent B acetonitrile
Gradientprofile: 100% A 1 min isocratic
  100% A---6 min--->100% B (linear or non linear gradient, curve 4)
  100% B 2 min isocratic
  100% A<---1 min----100% B (linear gradient)
  100% A 1 min isocratic
Stop Time (min) 10
Flow (ml/min) 1.0
Injection Volume (µl) 3
PDA parameters:
Start Wavelength (nm) 205
End Wavelength (nm) 350
Resolution (nm) 1.2
Sampling Rate (spectra/s) 1.000
Acquisition Stop Time (min) 9.00
MS parameters:

|  | Function 1 | Function 2 |
|---|---|---|
| Polarity | ES+ | ES− |
| Capillary (kV) | 3.50 | 3.50 |
| Cone (V) | 25.0 | 25.0 |
| Extractor (V) | 5.00 | 5.00 |
| RF Lens (V) | 0.1 | 0.1 |
| Source Temperature (° C.) | 130 | 130 |
| Desolvation Temperature (° C.) | 250 | 250 |
| Cone Gas Flow (L/Hr) | 50 | 50 |
| Desolvation Gas Flow (L/Hr) | 400 | 400 |
| LM Resolution | 15.0 | 15.0 |
| HM Resolution | 15.0 | 15.0 |
| Ion Energy | 0.5 | 0.5 |
| Multiplier (V) | 375 | 450 |
| Scan | 150-1200 | 150-1200 |
| Scan Duration (sec) | 0.5 | 0.5 |
| Interscan Delay (sec) | 0.3 | 0.3 |

ELSD parameters:
Evaporator (° C.) 80
Nebuliser (° C.) 80
Gas Flow (SLM) 0.8
Time Constant (sec) 3

EXAMPLE 2

Pharmacological Methods

In vitro inhibition of Kv1.3 potassium channels: the assay was used to determine the permeability of potassium ion channels expressed in the cell membrane. In cell culture, rubidium (Rb) can be used as a substitute for potassium due to comparable physico-chemical properties. Adherent CHO cells over-expressing the voltage gated potassium channel Kv1.3 were loaded with Rb. Depolarization of the cells leads to opening of the potassium channels and to efflux of Rb through the potassium channels. Thus, the Rb concentration in the supernatant is proportional to the potassium ion channel permeability. To identify potassium channel blockers, cells were incubated with compounds before depolarization. A reduction of Rb in the supernatant indicated the presence of a potassium ion channel blocker. The Rb concentration in the supernatant was measured using an Atomic Absorption Spectrometer.

CHO cells expressing either Kv1.3, Kv1.5 or hERG ion channels were cultured at 37° C./5% $CO_2$. Prior to the experiment cells were seeded in 96 well plates (Corning, N.Y., USA) and cultured for 24 h. Medium was discarded and replaced by 100 μl Rb buffer (10 mM HEPES pH 7.4, 5 mM Glucose, 5 mM RbCl, 140 mM NaCl, 2 mM $CaCl_2$, 1 mM $MgSO_4$) per well. After 4 h incubation the cells were washed three times with low potassium buffer (10 mM HEPES pH 7.4, 5 mM Glucose, 5 mM KCl, 140 mM NaCl, 2 mM $CaCl_2$, 1 mM $MgSO_4$). Compounds were dissolved in 75 μl low potassium buffer and added to the cells. After 12 minutes cells were depolarized by adding 75 μM high potassium buffer (10 mM HEPES pH 7.4, 5 mM Glucose, 145 mM KCl, 2 mM $CaCl_2$, 1 mM $MgSO_4$), followed by additional 15 minutes of incubation. The supernatant was transferred in a 96 well plate and the Rb concentration was measured using a ZEEnit Atomic Absorption Spectrometer (Analytik Jena, Germany). By comparing control vs. depolarized w/o compound, the ion channel inhibition was determined. Measurements were done in triplicate.

Experimental data (% Kv1.3 inhibition at $10^{-5}$ M) are given in the table in 'Example 5' (below).

EXAMPLE 3

General Aspects of Syntheses

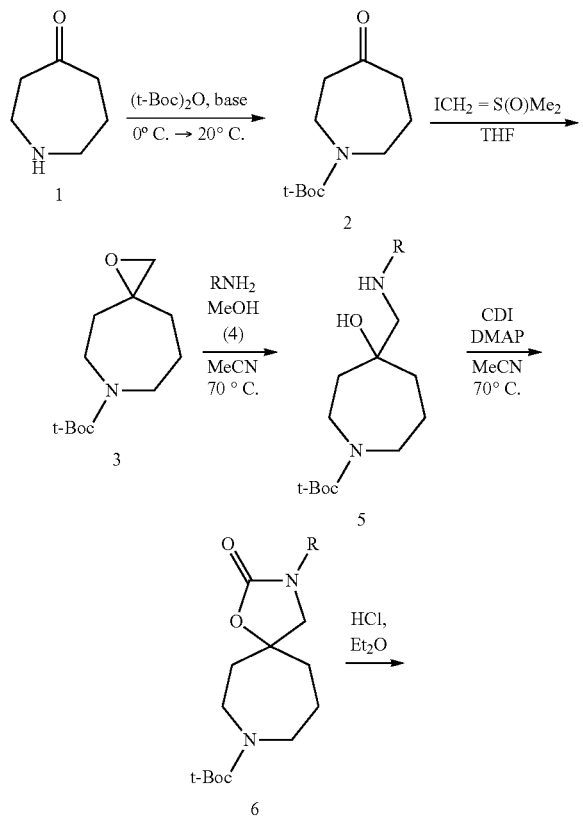

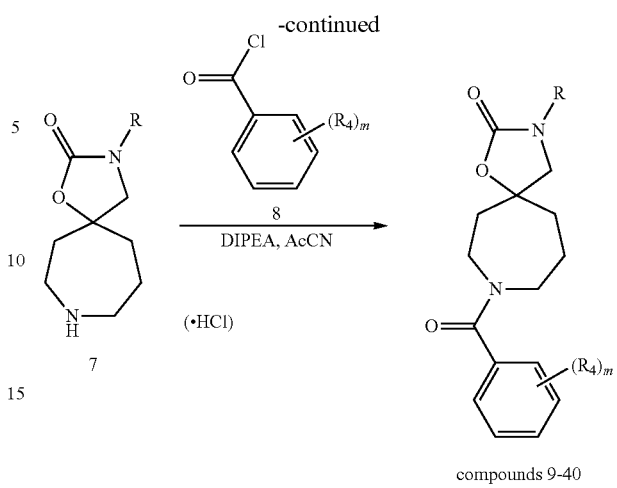

compounds 9-40

Hexahydro-(1H)-azepin-4-one 1 can be synthesized from the commercially available piperidin-4-one as described (Roglans, A. et al., *Synth. Commun.* 22, 1249-1258, 1992; Ashwood, M. S. et al., *J. Chem. Soc. Perkin Trans. 1*, 641-644, 1995). The amino group in 1 can be protected with a protecting group, such as the tert-Butyloxycarboyl (t-Boc) or benzyloxycarbonyl (Cbz) group to give a compound of formula 2. Preferably, such a protection is carried out in the presence of a base, such as aqueous sodium hydroxide or triethylamine in an inert organic solvent such as dichloromethane or methanol. The carbonyl moiety in compound 2 can be epoxidized to afford the epoxide 3, applying trimethyl sulfoxonium iodide in the presence of a base, such as sodium hydride. In this way, the pure epoxide 3 can be obtained in 4 steps from 4-piperidone without the need for any chromatographic purification steps.

The title compounds can be prepared by aminolysis of the spiro-epoxide 3 with amines of general formula 4, followed by ring-closure of the formed aminoalcohols 5 using a carbonylating agent such as carbonyldiimidazole (CDI). The presence of a small quantity of DMAP (e.g. 5 mol %) is preferred in this particular reaction to catalyze the conversion to the spiro oxazolidinone derivatives of general formula 6. This ring-closure reaction—wherein a [4,6]diazaspiro-undecane spirocycle is formed—in general proceeds more sluggishly in comparison with the analogous reaction for the formation of [4.5]diazaspirodecanes (Caroon, J. M. et al., *J. Med. Chem.* 1981, 24, 1320-1328). Preferably, traces of remaining starting material 4 are removed from the aminoalcohol 5 in order to increase the yields of the conversion of 5 to 6. The resulting spiro oxazolidinones 6 can be deprotected by acidic hydrolysis of the t-butyloxy carbonyl group, affording compounds of general formula 7. A Compound of general formula 7 can be reacted with a acetylating agent such as an acid chloride derivative of general formula 8 to give a compound of formula 9. Such a reaction is preferably carried out in an inert organic solvent such as acetonitrile in the presence of a base such as DIPEA or triethylamine in order to scavenge the liberated hydrochloric acid.

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using procedures well-known in the art, for example by mixing a compound of the present invention with a suitable acid, for instance an inorganic acid or an organic acid.

EXAMPLE 4

Syntheses of Intermediates t-Butyl hexahydro-4-oxo-(4H)-azepine-1-carboxylate (2): hexahydro-(4H)-azepin-4-one monohydrochloride (30 g, 200 mmol) was suspended in methanol (200 mL) and cooled to 0° C. Sodium hydroxide (8.02 g, 200 mmol) dissolved in water (20 ml) was added dropwise. Di-tert-butyl dicarbonate (Boc anhydride) (43.76 g, 200 mmol) was added portionwise and the resulting solution was stirred for 16 hours. The methanol was evaporated and the residue was dissolved in diethyl ether (400 ml) and water (200 ml). The organic layer was washed with water, dried ($MgSO_4$), filtrated and concentrated in vacuo, yielding crude 2 as a brown oil. Subsequent flash chromatograpic purification (ethyl acetate/petroleum ether) gave pure 2 (42 gram, 93%) as a pale yellow oil. 1H-NMR (400 MHz, CDCl3): δ 1.45 (s, 9H, tBu); 1.70-1.82 (m, 2H), 2.54-2.66 (m, 4H), 3.55-3.65 (m, 4H).

t-Butyl 1-oxa-6-azaspiro[2.6]nonane-6-carboxylate (3): to a stirred solution of trimethylsulfoxonium iodide (56.1 g, 255 mmol) in anhydrous DMSO (150 ml) was added a mixture of NaH (18.5 gram 1.5 equiv., 60% in mineral oil) under a nitrogen atmosphere. The mixture was stirred at 65° C. for 1 hour, whereafter compound 2 (32 g, 150 mmol) was added as a solution in DMSO (10 ml). The mixture was refluxed overnight under a nitrogen atmosphere. The solution was allowed to reach room temperature, water was added and the mixture was extracted with diethyl ether (3×200 ml). The combined organic layer was washed with $H_2O$, with brine and dried over $Na_2SO_4$. The $Et_2O$ was evaporated to yield 82.1 gram (32 g, 95%) compound 3. $^1$H-NMR (300 MHz, $CDCl_3$): δ (ppm)=1.45 (s, 9H, BOC); 1.50-2.10 (m, 6H), 2.60-2.70 (m, 2H), 3.5-3.60 (m, 2H).

t-Butyl 4-hydroxy-4-[(R-1-phenylethylamino)methyl]-1-azepanecarboxylate (5a) spiro-epoxide 3 (51.5 gram, 226 mmol) and (R)-(+)-1-phenylethyl amine (4a, 57.68 ml, 453 mmol) were dissolved in 300 mL MeOH/MeCN, 1/1 v/v. The solution was stirred at 60° C. for 48 hrs. The reaction was monitored by TLC ($CH_2Cl_2$/EtOH 9/1; Rf 5a 0.4). The reaction mixture was concentrated in vacuo on silica and purified by silica gel column chromatography (eluent: $CH_2Cl_2$/EtOH 95/5) to yield pure compound 5a (72 g, 90%) as an oil.

t-Butyl 3[(R)-1-phenyl-ethyl]-2-oxa-3,8-diazaspiro[4.6] undecane-8-carboxylate (6a): a solution of 5a (72 g, 206 mmol) in 1400 mL anhydrous MeCN was treated with 50.25 gram (1.5 equiv) of carbonyldiimidazole (CD) and stirred for 40 hrs at 70° C. under a nitrogen atmosphere. The solution was allowed to cool to ambient temperature and the reaction mixture was concentrated in vacuo on silica gel. The residue was purified by silica gel chromatography ($CH_2Cl_2$/EtOH 98/2). This yielded 66.0 gram (85.9%) of compound 6a.

3-[(R)-1-phenyl-ethyl]-1-oxa-3,8-diazaspiro[4.6]undecan-2-one (7a): to a suspension of compound 6a (21.1 g, 56 mmol) in water (10 ml) was added a 4M solution of hydrochloric acid in dioxane (70 ml). The mixture was stirred at 40° C. and subsequently for 16 hrs at room temperature. To the mixture was added dichloromethane (200 ml) and the solution was washed with NaHCO3 solution (5%, 100 ml). The water layer was extracted with DCM/MeOH, 9/1 (6×100 ml) and the combined organic layers was washed with water. The organic layer was evaporated to dryness to give compound 7a-HCl (12.2 g, 76%) as a white solid, used in the next step without further purification. $^1$H-NMR (300 MHz, ($CDCl_3$): δ (ppm)=1.55 (d, 3H), 1.6-2.3 (m, 6H), 2.9-3.25 (m, 6H), 5.25 (m, 1H, CH), 7.2-7.4 (m, 5H, H-arom).

3-[(S)-1-phenyl-ethyl]-1-oxa-3,8-diazaspiro[4.6]undecan-2-one 7 b: was prepared in a similar fashion as 7a starting from spiro epoxide 3 and (S)-(−)-1-phenylethyl amine 4b.

Preparation of the Optically Pure Diastereoisomers of 7a and 7b

Compounds 6a and 6b are mixtures of two diastereoisomers that were separated by chiral column chromatography. The protocol ("Method A") for the R-mixture 6a was different from the protocol ("Method B") used for the S-mixture 6b.

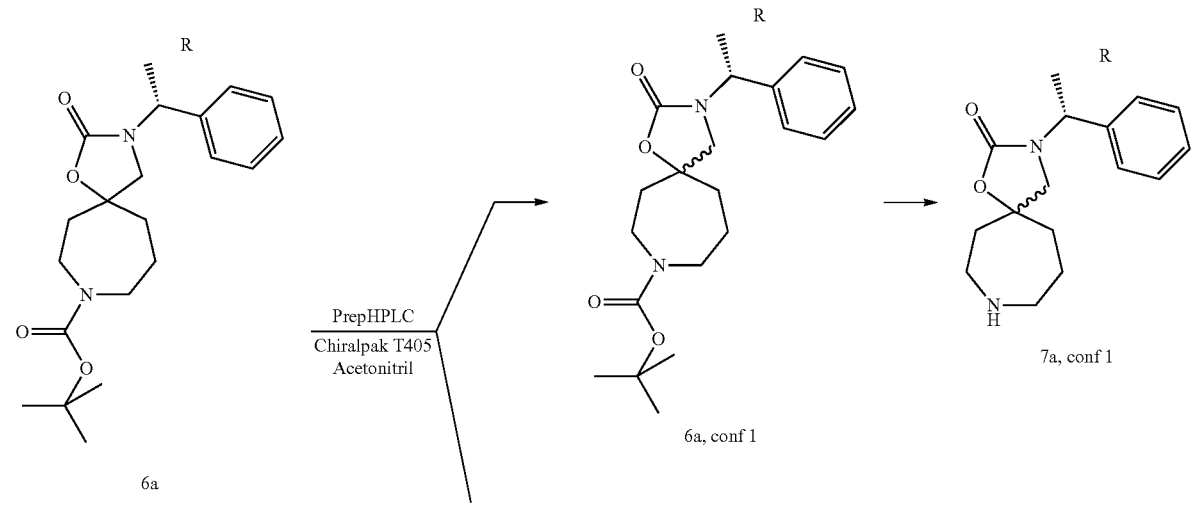

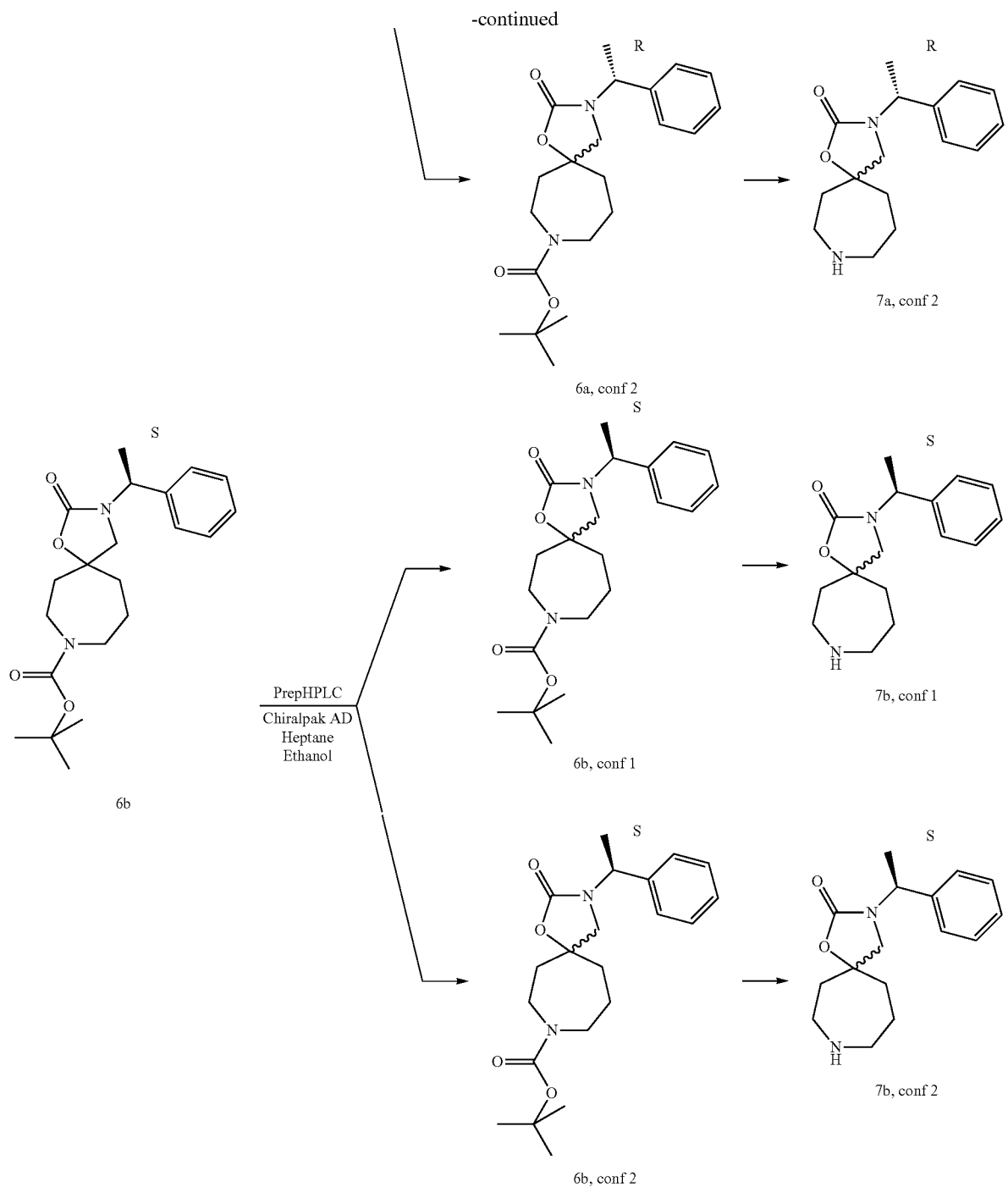

Method A for Mixture 6a.

A 33 g/L solution of compound 6a in acetonitrile was separated into the diastereomers 6a, (R,conf 1) and 6a (R,conf 2), using a preparative HPLC system. The preparative HPLC column (250*110 mm) was packed with Chiralpak T504®, 20 μm as stationary phase, and was equilibrated at room temperature and eluted using acetonitrile as mobile phase (570 ml/min). The load for the PrepHPLC-column was 0.07% m/m, and the run time approx. 10 min. Detection was performed using UV at a λ of 220 nm. The separation was checked by a chiral analytical system based on Chiralpak IC®, 5μ (250*4.6 mm) and Methyl-t-butyl-ether/ethanol mixture (95/5% V/V, 1 ml/min) at room temperature. Detection: UV, λ210 nm). The retention times from the analytical system were 9.7 and 11.8 min respectively.

Method B for Mixture 6b.

Using a preparative HPLC system, a 37 g/L solution of 6b in heptane/ethanol mixture (70/30% V/V) was separated in the diastereomers 6b (S,conf1) and 6b (S,conf2). The preparative HPLC column (250*76 mm) was packed with Chiralpak AD®, 20 μm as stationary phase and was equilibrated and eluted at room temperature using the mobile phase heptane/ethanol (70/30% V/V, 270 ml/min). The load for the PrepHPLC-column was 0.2% m/m and the run time approx.

12 min. Detection was performed by using UV at a λ of 220 nm. The separation was checked by a chiral analytical system based on Chiralpak AD-H®, 5µ (250*4.6 mm) and the same mobile phase (detection UV, λ210 nm) @1 ml/min and room temperature. The retention times from the analytical system were 5.2 and 8.2 min respectively Finally, deprotection of the intermediates 6a (R,conf1) and (R,conf2) and 6b (S,conf1) and (S,conf2) was established analogously as described above for the synthesis of the diastereoisomer mixtures 6a and 6b to give compounds 7a (R,conf1) and (R,conf2) and 7b (S,conf1) and (S,conf2). In this stage, the absolute configuration of the 7.5 fused ring system was not elucidated. Therefore, the chirality was named either conf1 or conf2.

EXAMPLE 5

Syntheses of Specific Compounds

The specific compounds of which the synthesis is described below are intended to further illustrate the invention in more detail, not to restrict the scope of the invention in any way. Other embodiments of the invention will be apparent to those skilled in the art from consideration of the specification and practice of the invention disclosed herein. The specification and examples must be considered as exemplary only. Synthesis of one specific example is described in full detail. All other preparations of the compounds 9 are performed in a similar fashion starting from the appropriate reagent 8 (acid chloride) and the corresponding intermediate 7.

8-(3,5-trifluoromethyl-benzoyl)-3-[(R)-1-phenyl-ethyl]-1-oxa-3,8-diazaspiro[4.6]undecan-2-one 31 (1R, conf 1)). To a solution of compound 7a (1R, conf1) (4.5 g, 15.9 mmol) and triethylamine (3.3 ml, 23.9 mmol) in ethyl acetate (80 ml) was slowly added and 3,5-(bis trifluoromethyl)benzoyl chloride (3.44 ml, 19.01 mmol). The mixture was stirred for 16 hrs at room temperature after which time TLC analysis showed complete reaction to one product (TLC eluent: DCM/MeOH, 99/1, v/v). Water was added (50 ml) and the water layer was extracted with DCM (2×100 ml). The combined organic layers was washed with water (100 ml), dried on MgSO$_4$ and evaporated to dryness. The residue was purified by silica gel column chromatography (eluent: DCM/MeOH, 99/1, v/v) to give compound 31 as an oil (7.7 g, 91%). LC-MS: room temperature 2.2 minutes, [M+H]$^+$ 515.1

Determination of the Absolute Chirality.

The absolute configuration of compounds 29-32 and 37-40 was determined by Vibrational Circular Dichroism. VCD is a type of vibrational spectroscopy that relies on the difference in a molecule's absorbance of left and right circularly polarized infrared radiation. The technique combines the structural specificity of IR spectroscopy with stereo chemical sensitivity. Enantiomers yield identical IR spectra but oppositely signed VCD spectra. The VCD spectrum of the compound was calculated using density functional theory, DFT. By comparing experimental and calculated spectra, the absolute configuration can be assigned (*Chemical and Engineering News, Jul.* 18, 2005, 32-33)

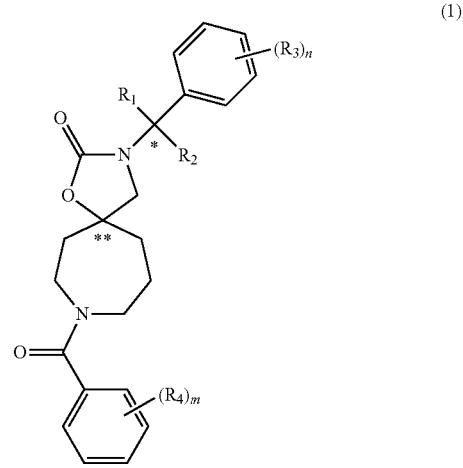

(1)

C*: configuration (R or S) of carbon atom to which R$_1$ and R$_2$ are attached

C**: configuration of the quaternary spiro-carbon atom: ±=diastereoisomeric mixture; 1=configuration 1; 2=configuration 2, R═R and S═S.

Physicochemical and pharmacological data were obtained using the protocols given above. R$_t$=LC-MS retention time; MH$^+$=MH$^+$ found, M=LC-MS method (H or W), %=percentage Kv1.3 inhibition at $10^{-5}$M

| N | R$_1$ | R$_2$ | C* | n | R$_3$ | C** | m | R$_4$ | R$_t$ | MH$^+$ | M | % |
|---|---|---|---|---|---|---|---|---|---|---|---|---|
| 9 | H | H | — | 0 | — | 1 | | α-naphthyl | 5.75 | 415.35 | H | 37 |
| 10 | H | H | — | 0 | — | 2 | | α-naphthyl | 5.75 | 415.35 | H | 89 |
| 11 | H | H | — | 1 | 4-Cl | ± | | α-naphthyl | 5.94 | 449.11 | H | 84 |
| 12 | H | H | — | 1 | 4-Cl | 1 | | α-naphthyl | 5.94 | 449.11 | H | 80 |
| 13 | H | H | — | 1 | 4-Cl | 2 | | α-naphthyl | 5.94 | 449.11 | H | 54 |
| 14 | CH$_3$ | CH$_3$ | — | 0 | — | ± | | α-naphthyl | 5.91 | 443.30 | H | 41 |
| 15 | CH$_3$ | H | S | 0 | — | ± | 2 | 3,5-diCF$_3$ | 2.32 | 515.20 | W | 81 |
| 16 | CH$_3$ | H | R | 0 | — | ± | 2 | 3,5-diCF$_3$ | 2.20 | 515.10 | W | 77 |
| 17 | CH$_3$ | H | S | 0 | — | ± | 1 | 3-Cl | 5.62 | 413.14 | H | 75 |
| 18 | CH$_3$ | H | S | 0 | — | ± | 1 | 3-CF$_3$ | 2.06 | 447.27 | W | 75 |
| 19 | CH$_3$ | H | S | 0 | — | ± | 1 | 4-CF$_3$ | 5.83 | 447.09 | H | 100 |
| 20 | CH$_3$ | H | S | 0 | — | ± | | α-naphthyl | 5.73 | 429.20 | H | 82 |
| 21 | CH$_3$ | H | S | 0 | — | ± | 1 | 3-OCF$_3$ | 2.12 | 463.22 | W | 98 |
| 22 | CH$_3$ | H | R | 0 | — | ± | 1 | 3-Cl | 5.64 | 413.19 | H | 68 |
| 23 | CH$_3$ | H | R | 0 | — | ± | 1 | 4-CF$_3$ | 5.83 | 447.21 | H | 72 |
| 24 | CH$_3$ | H | R | 0 | — | ± | | α-naphthyl | 5.75 | 429.25 | H | 79 |
| 25 | CH$_3$ | H | R | 0 | — | ± | 1 | 3-OCF$_3$ | 2.13 | 463.22 | W | 78 |
| 26 | CH$_3$ | H | S | 1 | 4-Cl | ± | 2 | 3,5-diCF$_3$ | 7.49 | 535.07 | H | 55 |
| 27 | CH$_3$ | H | R | 1 | 4-Cl | 1 | 2 | 3,5-diCF$_3$ | 6.55 | 548.13 | H | 80 |
| 28 | CH$_3$ | H | R | 1 | 4-Cl | 2 | 2 | 3,5-diCF$_3$ | 6.60 | 549.10 | H | 79 |
| 29 | CH$_3$ | H | S | 0 | — | S | 2 | 3,5-diCF$_3$ | 2.21 | 515.10 | W | 100 |
| 30 | CH$_3$ | H | S | 0 | — | R | 2 | 3,5-diCF$_3$ | 2.26 | 515.10 | W | 75 |

-continued

| N | R$_1$ | R$_2$ | C* | n | R$_3$ | C** | m | R$_4$ | R$_t$ | MH$^+$ | M | % |
|---|---|---|---|---|---|---|---|---|---|---|---|---|
| 31 | CH$_3$ | H | R | 0 | — | R | 2 | 3,5-diCF$_3$ | 2.19 | 515.10 | W | 64 |
| 32 | CH$_3$ | H | R | 0 | — | S | 2 | 3,5-diCF$_3$ | 2.23 | 515.10 | W | 99 |
| 33 | CH$_3$ | CH$_3$ | — | 1 | 4-Cl | ± | 2 | 3,5-diCF$_3$ | 6.69 | 562.15 | H | 6 |
| 34 | CH$_3$ | H | S | 1 | 4-Cl | 1 | 2 | 3,5-diCF$_3$ | 6.55 | 549.18 | H | 87 |
| 35 | CH$_3$ | H | S | 1 | 4-Cl | 2 | 2 | 3,5-diCF$_3$ | 6.61 | 549.19 | H | 6 |
| 36 | H | H | — | 0 | — | ± | | α-naphthyl | 5.75 | 415.35 | H | 92 |
| 37 | CH$_3$ | H | R | 0 | — | R | 1 | 3-cyano | 1.75-78 | 404.20 | W | — |
| 38 | CH$_3$ | H | R | 0 | — | S | 1 | 3-cyano | 1.77 | 404.20 | W | — |
| 39 | CH$_3$ | H | S | 0 | — | S | 1 | 3-cyano | 1.75 | 404.20 | W | — |
| 40 | CH$_3$ | H | S | 0 | — | R | 1 | 3-cyano | 1.75 | 404.20 | W | — |

EXAMPLE 6

Pharmaceutical Preparations

For clinical use, compounds of formula (1) are formulated into pharmaceutical compositions, which are novel embodiments of the invention because they contain the compounds, more particularly specific compounds disclosed herein. Types of pharmaceutical compositions that may be used include: tablets, chewable tablets, capsules (including microcapsules), solutions, parenteral solutions, ointments (creams and gels), suppositories, suspensions, and other types disclosed herein, or are apparent to a person skilled in the art from the specification and general knowledge in the art. The active ingredient for instance, may also be in the form of an inclusion complex in cyclodextrins, their ethers or their esters. The compositions are used for oral, intravenous, subcutaneous, tracheal, bronchial, intranasal, pulmonary, transdermal, buccal, rectal, parenteral or other ways to administer. The pharmaceutical formulation contains at least one compound of formula (1) in admixture with at least one pharmaceutically acceptable adjuvant, diluent and/or carrier. In embodiments of the present invention, the total amount of active ingredients can be in the range of from about 0.1% (w/w) to about 95% (w/w) of the formulation, such as from 0.5% to 50% (w/w) and preferably from 1% to 25% (w/w). In some embodiments, the amount of active ingredient can be greater than about 95% (w/w) or less than about 0.1% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet can be prepared using the ingredients below:

| Ingredient | Quantity (mg/tablet) |
|---|---|
| COMPOUND 10 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy.

Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating a condition in which blocking of voltage gated Kv1.3 potassium channel is required or desired, and methods of medical treatment, comprise the administration of a therapeutically effective total amount of at least one compound of formula (1) to a patient suffering from, or susceptible to, a condition in which blocking of voltage gated Kv1.3 potassium channel is required or desired.

The invention claimed is:

1. A compound of formula (1):

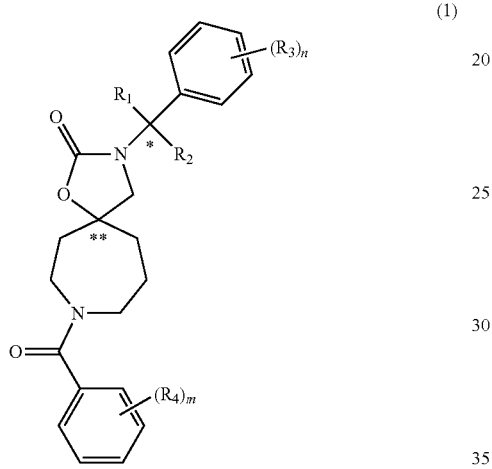

(1)

wherein:
each of $R_1$ and $R_2$ is chosen from hydrogen, deuterium, fluorine, $CF_3$, and alkyl($C_{1-3}$), which may be unsubstituted or substituted with one or more fluorine atoms,
n is an integer chosen from 0, 1, and 2,
$R_3$ is chosen from halogen, alkyl($C_{1-3}$), $CF_3$, CN, $NH_2$, NHAc, OH, $OCH_3$, and $OCF_3$,
m is an integer chosen from 0, 1, 2, and 3, and
$R_4$ is chosen from halogen, alkyl($C_{1-3}$), $CF_3$, CN, $NH_2$, NHAc, OH, $OCH_3$, and $OCF_3$, or
$(R_4)_m$ and the phenyl ring to which it is attached form a naphthyl group,
or a tautomer, a stereoisomer, or a pharmacologically acceptable salt of any of the foregoing.

2. A compound according to claim 1, wherein each of $R_1$ and $R_2$ are hydrogen or methyl, n is 0 or 1, $R_3$ is halogen, m is 1 or 2, and $R_4$ is chosen from halogen, $CF_3$, CN, $OCH_3$, and $OCF_3$, or $(R_4)_m$ and the phenyl ring to which it is attached form a naphthyl group.

3. A compound according to claim 1, wherein the compound is chosen from:
(5S)-8-[3,5-bis(trifluoromethyl)benzoyl]-3-[(1S)-1-phenylethyl]-1-oxa-3,8-diazaspiro[4.6]-undecan-2-one,
(5R)-8-[3,5-bis(trifluoromethyl)benzoyl]-3-[(1S)-1-phenylethyl]-1-oxa-3,8-diazaspiro[4.6]-undecan-2-one,
(5R)-8-[3,5-bis(trifluoromethyl)benzoyl]-3-[(1R)-1-phenylethyl]-1-oxa-3,8-diazaspiro[4.6]-undecan-2-one,
(5S)-8-[3,5-bis(trifluoromethyl)benzoyl]-3-[(1R)-1-phenylethyl]-1-oxa-3,8-diazaspiro[4.6]-undecan-2-one,
(5S)-8-[3-cyanobenzoyl]-3-[(1S)-1-phenylethyl]-1-oxa-3,8-diazaspiro[4.6]undecan-2-one,
(5R)-8-[3-cyanobenzoyl]-3-[(1S)-1-phenylethyl]-oxa-3,8-diazaspiro[4.6]undecan-2-one,
(5R)-8-[3-cyanobenzoyl]-3-[(1R)-1-phenylethyl]-1-oxa-3,8-diazaspiro[4.6]undecan-2-one, and
(5S)-8-[3-cyanobenzoyl]-3-[(1R)-1-phenylethyl]-1-oxa-3,8-diazaspiro[4.6]undecan-2-one.

4. A compound according to claim 1, wherein said compound is an optically active enantiomer or diastereoisomer.

5. A compound according to claim 1, wherein the carbon atom attached to the nitrogen atom of the oxazolinone ring is the (R) or (S) enantiomer.

6. A compound according to claim 1, wherein the central quaternary spiro-carbon atom is the (R) or (S) enantiomer.

7. A compound of formula (v):

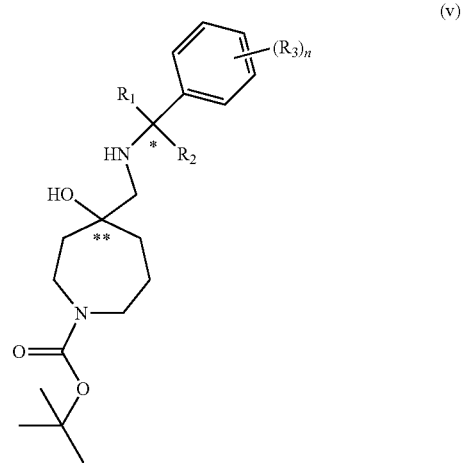

(v)

wherein
each of $R_1$ and $R_2$ is chosen from hydrogen, deuterium, fluorine, $CF_3$, and alkyl($C_{1-3}$), which may be unsubstituted or substituted with one or more fluorine atoms,
n is an integer chosen from 0, 1, and 2, and
$R_3$ is chosen from halogen, alkyl($C_{1-3}$), $CF_3$, CN, $NH_2$, NHAc, OH, $OCH_3$, and $OCF_3$.

8. A compound of formula (vi):

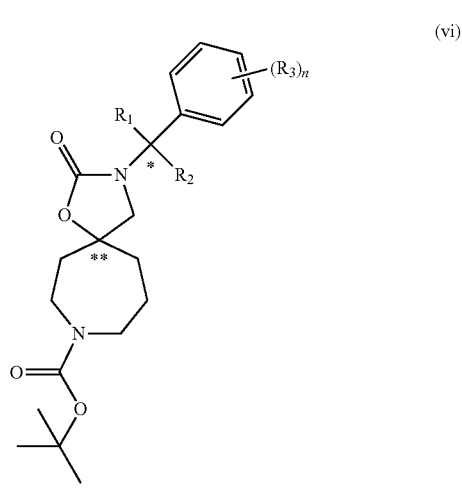

(vi)

wherein
each of $R_1$ and $R_2$ is chosen from hydrogen, deuterium, fluorine, $CF_3$, and alkyl($C_{1-3}$), which may be unsubstituted or substituted with one or more fluorine atoms,
n is an integer chosen from 0, 1, and 2, and
$R_3$ is chosen from halogen, alkyl($C_{1-3}$), $CF_3$, CN, $NH_2$, NHAc, OH, $OCH_3$, and $OCF_3$.

9. A compound of formula (vii):

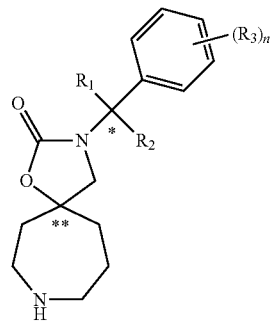

(vii)

wherein
each of $R_1$ and $R_2$ is chosen from hydrogen, deuterium, fluorine, $CF_3$, and alkyl($C_{1-3}$), which may be unsubstituted or substituted with one or more fluorine atoms,
n is an integer chosen from 0, 1, and 2, and
$R_3$ is chosen from halogen, alkyl($C_{1-3}$), $CF_3$, CN, $NH_2$, NHAc, OH, $OCH_3$, and $OCF_3$,
with the proviso that the compound of formula (vii) is not 3-[(S)-1-phenyl-ethyl]-1-oxa-3,8-diazaspiro[4.6]undecan-2-one.

10. A compound according to claim 9, wherein the compound is:

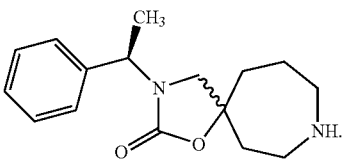 [SMILES: C[C@H](c1ccccc1)N1CC2(CCCNCC2)OC1=O]

11. A method for preparing a compound according to claim 1, the method comprising:
(i) protecting the amino group of hexahydro(1H)-azepin-4-one with a protecting group, yielding a ketone of formula 2:

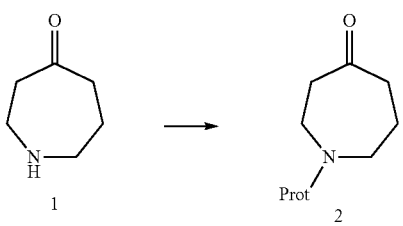

(ii) epoxidizing the ketone of formula 2 to a spiro-epoxide of formula 3:

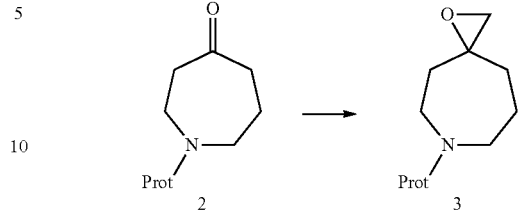

(iii) aminolysing of the spiro-expoxide of formula 3, with an amine 4 of formula $RNH_2$, wherein R represents the moiety:

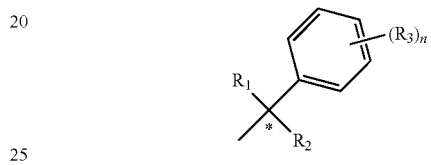

and wherein each of $R_1$ and $R_2$ is chosen from hydrogen, deuterium, fluorine, $CF_3$, and alkyl($C_{1-3}$), which may be unsubstituted or substituted with one or more fluorine atoms; n is an integer chosen from 0, 1, and 2; $R_3$ is chosen from halogen, alkyl($C_{1-3}$), $CF_3$, CN, $NH_2$, NHAc, OH, $OCH_3$, and $OCF_3$; m is an integer chosen from 0, 1, 2, and 3, to yield an aminoalcohol of formula 5:

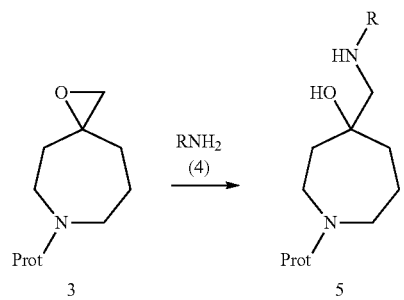

(iv) ring closing of the aminoalcohol of formula 5, in the presence of a carbonylating agent, catalyzed by DMAP, to yield the spiro-oxazolidinone derivative of formula 6, and

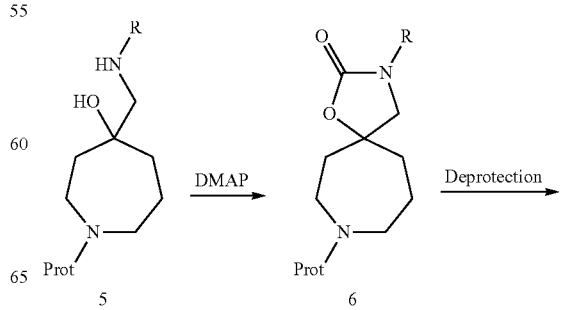

-continued

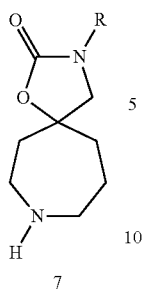

7

(v) deprotecting the spiro-oxazolidinone of formula 6, yielding a compound of formula 7.

12. The method according to claim 11, wherein said protecting group is chosen from a benzyloxycarbonyl (Cbz) and a tert-butoxycarbonyl (t-Boc) group.

13. A method for treating at least one condition chosen from diabetes, psoriasis, obesity, transplant rejection, and inflammatory neuropathies, -cell mediated autoimmune diseases, rheumatoid arthritis, and multiple sclerosis, the method comprising administering a compound of formula (1) to a patient in need of such treatment, wherein the compound of formula (1) is:

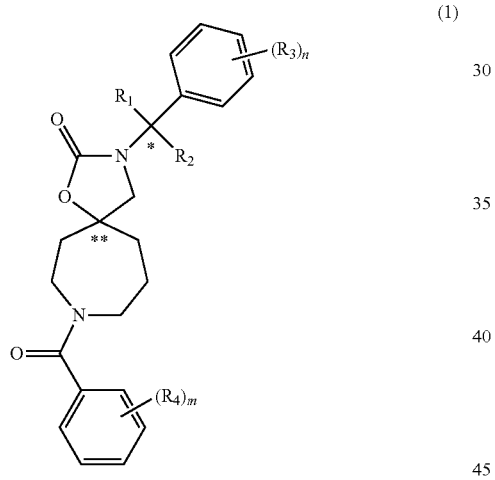

(1)

wherein:
each of $R_1$ and $R_2$ is chosen from hydrogen, deuterium, fluorine, $CF_3$, and alkyl($C_{1-3}$), which may be unsubstituted or substituted with one or more fluorine atoms, n is an integer chosen from 0, 1, and 2,
$R_3$ is chosen from halogen, alkyl($C_{1-3}$), $CF_3$, CN, $NH_2$, NHAc, OH, $OCH_3$, and $OCF_3$,
m is an integer chosen from 0, 1, 2, and 3, and
$R_4$ is chosen from halogen, alkyl($C_{1-3}$), $CF_3$, CN, $NH_2$, NHAc, OH, $OCH_3$, and $OCF_3$, or
$(R_4)_m$ and the phenyl ring to which it is attached form a naphthyl group,
or a tautomer, a stereoisomer, or a pharmacologically acceptable salt of any of the foregoing.

14. A pharmaceutical composition comprising at least one pharmaceutically acceptable carrier, or at least one pharmaceutically acceptable auxiliary substance, or a combination of two or more thereof; and a pharmacologically active amount of at least one compound of formula (1):

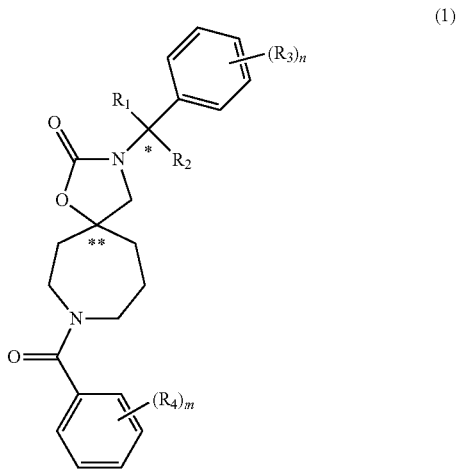

(1)

or a pharmacologically acceptable salt thereof, wherein:
each of $R_1$ and $R_2$ are chosen from hydrogen, deuterium, fluorine, $CF_3$, and alkyl($C_{1-3}$), unsubstituted or substituted with one or more fluorine atoms,
n is an integer chosen from 0, 1, and 2, $R_3$ is chosen from halogen, alkyl($C_{1-3}$), $CF_3$, CN, $NH_2$, NHAc, OH, $OCH_3$, and $OCF_3$,
m is an integer chosen from 0, 1, 2, and 3, and
$R_4$ is chosen from halogen, alkyl($C_{1-3}$), $CF_3$, CN, $NH_2$, NHAc, OH, $OCH_3$, and $OCF_3$, or
$(R_4)_m$ and the phenyl ring to which it is attached form a naphthyl group.

* * * * *